United States Patent [19]

Summers et al.

[11] Patent Number: 4,822,809

[45] Date of Patent: Apr. 18, 1989

[54] BENZAZOLE LIPOXYGENASE INHIBITING COMPOUNDS

[75] Inventors: James B. Summers; Andrew O. Stewart, both of Libertyville, Ill.

[73] Assignee: Abbott Laboratories, Abbott Park, Ill.

[21] Appl. No.: 120,251

[22] Filed: Nov. 13, 1987

[51] Int. Cl.$^4$ .................. A61K 31/425; C07D 277/64
[52] U.S. Cl. ..................... 514/367; 514/375; 514/395; 548/178; 548/180; 548/217; 548/330
[58] Field of Search ............... 548/330, 178, 180, 217; 514/367, 375, 395

[56] References Cited

U.S. PATENT DOCUMENTS

| 3,855,242 | 12/1974 | Chapman et al. | 549/57 |
| 3,912,748 | 10/1975 | Evans et al. | 548/224 |
| 4,112,186 | 10/1978 | Lafon | 548/330 X |
| 4,594,425 | 6/1986 | Musser et al. | 548/161 |
| 4,604,407 | 8/1986 | Haslanger et al. | 514/575 |
| 4,607,053 | 8/1986 | Karanewsky et al. | 514/575 |
| 4,665,206 | 5/1987 | Redpath et al. | 549/51 |

FOREIGN PATENT DOCUMENTS 0196184 10/1986 European Pat. Off.
1231804 5/1971 United Kingdom.

Primary Examiner—Richard A. Schwartz
Attorney, Agent, or Firm—Steven R. Crowley; Steven F. Weinstock; Martin L. Katz

[57] ABSTRACT

Compounds of the formula:

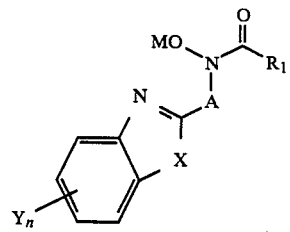

wherein $R_1$ is (1) hydrogen, (2) $C_1$ to $C_4$ alkyl, (3) $C_2$ to $C_4$ alkenyl, or (4) $NR_2R_3$, wherein $R_2$ and $R_3$ are independently selected from (1) hydrogen, (2) $C_1$ to $C_4$ alkyl and (3) hydroxyl, but $R_2$ and $R_3$ are not simultaneously hydroxyl;

X is (1) oxygen, (2) sulfur, (3) $SO_2$, or (4) $NR_4$, wherein $R_4$ is (1) hydrogen, (2) $C_1$ to $C_6$ alkyl, (3) $C_1$ to $C_6$ alkyl or (4) aroyl;

A is selected from $C_1$ to $C_6$ alkylene and $C_2$ to $C_6$ alkenylene; n is 0-4;

Y is selected independently at each occurrence from (1) hydrogen, (2) halogen, (3) hydroxy, (4) cyano, (5) halosubstituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) aryl, (11) aryloxy, (12) aroyl, (13) $C_1$ to $C_{12}$ arylalkyl, (14) $C_2$ to $C_{12}$ arylalkenyl, (15) $C_1$ to $C_{12}$ arylalkoxy, (16) $C_1$ to $C_{12}$ arylthioalkoxy, and substituted derivatives of (17) aryl, (18) aryloxy, (19) aroyl, (20) $C_1$ to $C_{12}$ arylalkyl, (21) $C_2$ to $C_{12}$ arylalkenyl, (22) $C_1$ to $C_{12}$ arylalkoxy, or (23) $C_1$ to $C_{12}$ arylthioalkoxy, wherein substituents are selected from halo, nitro, cyano, $C_1$ to $C_{12}$ alkyl, alkoxy, and halosubstituted alkyl;

and M is hydrogen, a pharmaceutically acceptable cation, aroyl, or $C_1$ to $C_{12}$ alkoyl, are potent inhibitors of 5- and/or 12-lipoxygenase enzymes. Also disclosed are lipoxygenase inhibiting compositions and a method for inhibiting lipoxygenase.

12 Claims, No Drawings

BENZAZOLE LIPOXYGENASE INHIBITING COMPOUNDS

TECHNICAL FIELD

This invention relates to organic compounds which inhibit lipoxygenase enzymes. It also relates to methods and compositions for inhibiting lipoxygenase enzymes in human and animal hosts in need of such treatment.

BACKGROUND OF THE INVENTION

The lipoxygenases are a family of enzymes which catalyze the oxygenation of arachidonic acid. The enzyme 5-lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes (LTs).

Similarly, 12- and 15-lipoxygenase convert arachidonic acid to 12- and 15-HPETE, respectively. Biochemical reduction of 12-HPETE leads to 12-HETE, while 15-HPETE is the precursor of the class of biological agents known as the lipoxins.

A variety of biological effects are associated with these products from lipoxygenase metabolism of arachidonic acid and they have been implicated as mediators in various disease states. For example, the LTs $C_4$ and $D_4$ are potent constrictors of human airways in vitro, and aerosol administration of these substances to non-asthmatic volunteers induces broncho-constriction. $LTB_4$ and 5-HETE are potent chemotactic factors for inflammatory cells such as polymorphonuclear leukocytes. They also have been found in the synovial fluid of rheumatoid arthritic patients. Leukotrienes have also been implicated as important mediators in allergic rhinitis, psoriasis, adult respiratory distress syndrome. Crohn's disease, endotoxin shock, and ischemia induced myocardial injury among others. The biological activity of the LTs has been reviewed by Lewis and Austen (J. Clinical Invest. 73, 889, 1984 and by J. Sirois (Adv. Lipid Res. 21, 78, 1985).

The product 12-HETE has been found in high levels in epidermal tissue of patients with psoriasis. The lipoxins have recently been shown to stimulate elastase and superoxide ion release from neutrophils.

Thus, lipoxygenase enzymes are believed to play an important role in the biosynthesis of mediators of asthma, allergy, arthritis, psoriasis, and inflammation. Blocking these enzymes interrupts the biochemical pathways believed to be involved in these disease states.

DETAILED DESCRIPTION OF THE INVENTION

In accordance with the present invention, there are 5- and/or 12-lipoxygenase inhibiting compounds of the formula:

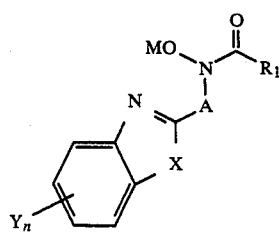

Formula I wherein $R_1$ is (1) hydrogen, (2) $C_1$ to $C_4$ alkyl, (3) $C_2$ $C_4$ alkenyl, or (4) $NR_2R_3$, wherein $R_2$ and $R_3$ are independently selected from (1) hydrogen, (2) $C_1$ to $C_4$ alkyl and (3) hydroxyl, but $R_2$ and $R_3$ are not simultaneously hydroxyl;

X is (1) oxygen, (2) sulfur, (3) $SO_2$, or (4) $NR_4$ wherein $R_4$ is (1) hydrogen, (2) $C_1$ to $C_6$ alkyl, (3) $C_1$ to $C_6$alkoyl or (4) aroyl;

A is selected from $C_1$ to $C_6$alkylene and $C_2$ to $C_6$alkenylene;

Y is independently selected at each occurrence from (1) hydrogen, (2) halogen, (3) hydroxy, (4) cyano, (5) halosubstituted alkyl, (6) $C_1$ to $C_{12}$alkyl, (7) $C_2$ to $C_{12}$alkenyl, (8) $C_1$ to $C_{12}$alkoxy, (9) $C_3$ to $C_8$ cycloalkyl, (10) aryl, (11) aryloxy, (12) aroyl, (13) $C_1$ to $C_{12}$arylalkyl, (14) $C_2$ to $C_{12}$arylalkenyl, (15) $C_1$ to $C_{12}$arylalkoxy, (16) $C_1$ to $C_{12}$arylthioalkoxy, and substituted derivatives of (17) aryl, (18) aryloxy, (19) aroyl, (20) $C_1$ to $C_{12}$arylalkyl, (21) $C_2$ to $C_{12}$arylalkenyl, (22) $C_1$ to $C_{12}$arylalkoxy, or (23) $C_1$ to $C_{12}$arylthioalkoxy, wherein substituents are selected from halo, nitro, cyano, $C_1$ to $C_{12}$alkyl, alkoxy, and halosubstituted alkyl; the number n is 0–4; the group(s) Y may be substituted from any of the positions on the aryl ring;

and M is hydrogen, a pharmaceutically acceptable cation, aroyl, or $C_1$ to $C_{12}$alkoyl.

Examples of compounds which are themselves within the scope of the present invention including the following:

N-hydroxy-N-(1-methyl-benzo[b]imidazol-2-ylmethyl)N'-methyl urea

N-hydroxy-N-(1-benzo[b]thiazol-2-ylethyl)urea

N-hydroxy-N-(1-benzo[b]oxoazol-2-ylethyl)urea

N-hydroxy-N-(benzo[b]oxazol-2-ylmethyl)N'-1-methylethyl urea

N-hydroxy-N-(1-benzo[b]oxazol-2-ylethyl)N',N'-dimethyl urea

N-hydroxy-N-(1-benzo[b]oxazol-2-ylethyl)N'-hydroxy urea

N-hydroxy-N-(1-benzo[b]thiazol-2-ylethyl)acetamide

N-hydroxy-N-(benzo[b]oxazol-2-ylmethyl)methylpropionamide

N-hydroxy-N-[(1-ethylbenzo[b]imidazol-2-yl)methyl]-propenamide

N-hydroxy-N-(1-methyl-1-benzo[b]oxazol-2-ylethyl)urea

N-hydroxy-N-(2-benzo[b]oxazol-2-ylethyl)urea

N-hydroxy-N-(1-methylethyl-2-benzo[b]oxazol-2-ylethyl)acetamide

N-hydroxy-N-[3-(6-phenoxybenzo[b]oxazol-2-yl)propyl]urea

N-hydroxy-N-(3-benzo[b]thiazol-2-ylprop-2-enyl)urea

N-hydroxy-N-(1-methyl-3benzo[b]oxazol-2-enyl)urea

N-hydroxy-N-[1-(4-methoxy-benzo[b]imidazol-2-yl)ethyl]urea

N-hydroxy-N-[1-(1-acetylbenzo[b]imidazol-2-yl)ethyl]urea

N-hydroxy-N-[1-(1-benzoylbenzo[b]imidazol-2-yl)ethyl]urea

N-hydroxy-N-(1-benzo[b]thiazol-2-ylethyl)urea 3,3-dioxide

N-hydroxy-N-[1-(5-fluorobenzo[b]oxazol-2-yl)ethyl]urea

N-hydroxy-N-[1-(7-hydroxybenzo[b]oxazol-2-yl)ethyl]urea

N-hydroxy-N-[6-trifluoromethyl-(1-benzo[b]oxazol-2-yl)ethyl]urea

N-hydroxy-N-[1-(5,6-dimethylbenzo[b]oxazol-2-yl)ethyl]urea
N-hydroxy-N-[1-(6-(4-fluorophenyl)benzo[b]thiazol-2-yl)ethyl]urea
N-hydroxy-N-[1-(5-phenylmethoxybenzo[b]oxazol-2-yl)ethyl]urea
N-hydroxy-N-(6-phenylmethylbenzo[b]thiazol-2-ylmethyl)N'methyl urea
N-hydroxy-N-[4-(3,5-bistrifluoromethylbenzoyl)-1-benzo[b]oxazol-2-ylethyl]urea
N-hydroxy-N-(1-benzo[b]thiazol-2-ylethyl)urea sodium salt
N-hydroxy-N-(1-benzo[b]thiazol-2-ylethyl)urea ammonium salt
N-hydroxy-N-(1-benzo[b]thiazol-2-ylethyl)urea tetrabutylammonium salt
N-butyroxy-N-(1-benzo[b]thiazol-2-ylethyl)urea The term "alkylene" is used herein to mean straight or branched chain spacer radicals such as —$CH_2$—, —$CHCH_3$—, —$C(CH_3)_2$—, —$CH(C_2H_5)$—, —$CH_2CH_2$—, —$CH_2CHCH_3$—, $C(CH_3)_2C(CH_3)_2$—, $CH_2CH_2CH_2$ and the like.

The term "alkenylene" is used herein to mean straight or branched chain unsaturated spacer radicals such as —CH=CH—, —CH=$CHCH_2$—, CH=CH$CH(CH_3)$—, —$C(CH_3)$=$CHCH_2$—, —$CH_2$CH=CH$CH_2$—, $C(CH_3)_2$CH=CHC$(CH_3)_2$—, and the like.

The term "alkyl" is used herein to mean straight or branched chain radicals of 1 to 12 carbon atoms, including, but not limited to methyl, ethyl, n-propyl, isopropyl, n-butyl, sec-butyl, isobutyl, tert-butyl, and the like.

The term "alkenyl" is used herein to mean straight or branched chain unsaturated radicals of 2 to 12 carbon atoms, including, but not limited to ethenyl, 1-propenyl, 2-propenyl, 2-methyl-1-propenyl, 1-butenyl, 2-butenyl, and the like.

The term "cycloalkyl" is used herein to mean cyclic radicals, preferably 3 to 8 carbons, including, but not limited to cyclopropyl, cyclobutyl, cyclopentyl, cyclohexyl, and the like.

The term "alkoxy" is used herein to mean —$OR_5$ wherein $R_5$ is an alkyl radical, including, but not limited to methoxy, ethoxy, isopropoxy, n-butoxy, sec-butoxy, isobutoxy, tert-butoxy, and the like.

The term "alkoyl" is used herein to mean —$COR_6$ wherein $R_6$ is an alkyl radical, including, but not limited to formyl, acetyl, propionyl, butyryl, isobutyryl, pivaloyl, and the like.

The term "carboalkoxy" is used herein to mean —$COR_7$ wherein $R_7$ is an alkoxy radical, including, but not limited to carbomethoxy, carboethoxy, carboisopropoxy, carbobutoxy, carbosec-butoxy, carboisobutoxy, carbotert-butoxy, and the like.

The term "aryl" is used herein to mean substituted and unsubstituted aromatic radicals wherein the substituents are chosen from halo, nitro, cyano, $C_1$ to $C_{12}$alkyl, alkoxy, and halosubstituted alkyl, including, but not limited to phenyl, 1- or 2-naphthyl, and the like.

The term "aroyl" is used herein to mean —$COR_8$ wherein $R_8$ is an aryl radical, including, but not limited to benzoyl, 1-naphthoyl, 2-naphthoyl, and the like.

The term "aryloxy" is used herein to mean —$OR_9$ wherein $R_9$ is an aryl radical, including, but not limited to phenoxy, 1-naphthoxy, 2-naphthoxy, and the like.

The term "arylalkoxy" is used herein to mean —$OR_{10}$ wherein $R_{10}$ is an arylalkyl radical, including, but not limited to phenylmethoxy (i.e., benzyloxy), 4-fluorobenzyloxy, 1-phenylethoxy, 2-phenylethoxy, diphenylmethoxy, 1-naphthylmethyloxy, 2-napthylmethyloxy, 9-fluorenoxy, 2-, 3- or 4-pyridylmethoxy, 2-, 3-, 4-, 5-, 6-, 7-, 8-quinolylmethoxy and the like.

The term "arylthioalkoxy" is used herein to mean —$SR_{11}$ wherein $R_{11}$ is an arylalkyl radical, including, but not limited to phenylthiomethoxy (i.e., thiobenzyloxy), 4-fluorothiobenzyloxy, 1-phenylthioethoxy, 2-phenylthioethoxy, diphenylthiomethoxy, 1-naphthylthiomethoxy and the like.

The term "arylalkyl" is used herein to mean an aryl group appended to an alkyl radical, including, but not limited to phenylmethyl (benzyl), 1-phenylethyl, 2-phenylethyl, 1-naphthylethyl and the like.

The term "arylalkenyl" is used herein to mean an aryl group appended to an alkenyl radical, including, but not limited to phenylethenyl, 3-phenylprop-1-enyl, 3-phenylprop-2-enyl, 1-naphthylethenyl and the like.

The terms "halo" and "halogen" are used herein to mean radicals derived from the elements fluorine, chlorine, bromine, or iodine.

The term "halosubstituted alkyl" refers to an alkyl radical as described above substituted with one or more halogens, including, but not limited to chloromethyl, trifluoromethyl, 2,2,2-trichloroethyl, and the like.

The term "pharmaceutically acceptable cation" refers to non-toxic cations including but not limited to cations based on the alkali and alkaline earth metals, such as sodium, lithium, potassium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "lipoxygenase" is used herein to mean 5- and/or 12-lipoxygenase.

The compounds of the invention inhibit lipoxygenase, which makes the compounds useful in the treatment and prevention of disease states wherein lipoxygenase may be involved, including, but not limited to, asthma, rheumatoid arthritis, gout, psoriasis, allergic rhinitis, adult respiratory distress syndrome, Crohn's disease, endotoxin shock, inflammatory bowel disease and/or ischemia induced myocardial or brain injury.

METHOD OF TREATMENT

This invention also provides a method of treatment of inhibiting 5- and/or 12-lipoxygenase activity in a human or lower animal host in need of such treatment which method comprises administration to the human or lower animal host of a compound of the invention in a therapeutically effective amount to inhibit lipoxygenase activity in the host. This invention also provides a method of treating asthma, rheumatoid arthritis, gout, psoriasis, allergic rhinitis, adult respiratory distress syndrome, Crohn's disease, endotoxin shock, and/or ischemia-induced myocardial injury in a human or lower animal in need of such treatment comprising administering to the human or lower animal a therapeutically effective amount of a compound described above. Further, this invention provides a method of threating or preventing the symptoms of the disease states mentioned above.

The compounds of the present invention may be administered orally, parenterally or topically in dosage unit formulations containing conventional nontoxic pharmaceutically acceptable carriers, adjuvants and vehicles as desired.

The term parenteral as used herein includes a subcutaneous, intravenous, intraaerterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from about 0.001 to about 100 mg/kg body weight daily and more usually 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

FORMULATION OF PHARMACEUTICAL COMPOSITION

This invention also provides for compositions in unit dosage form for the inhibition of 5- or 12-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the composition of this invention, as available in the pharmaceutical arts. Injectable preparations, such as oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile nonpyrogenic water or 1,3-butanediol. Among the other acceptable vehicles and solvents that may be employed are 5% dextrose injection. Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compound of this invention can be prepared by mixing the drug with suitable nonirritating excipient such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

SYNTHESIS OF THE COMPOUNDS

Several synthetic methods may be used to prepare compounds of this invention. Some of these methods are described by schemes 1-5 below. Although in each case the sequence is illustrated with a compound of formula I wherein $R_1$ is methyl or $NH_2$, A is —CHCH$_3$—, X is sulfur and Y is hydrogen, it will be seen from the examples the other compounds of this invention can be prepared in the same manner using the appropriate starting materials.

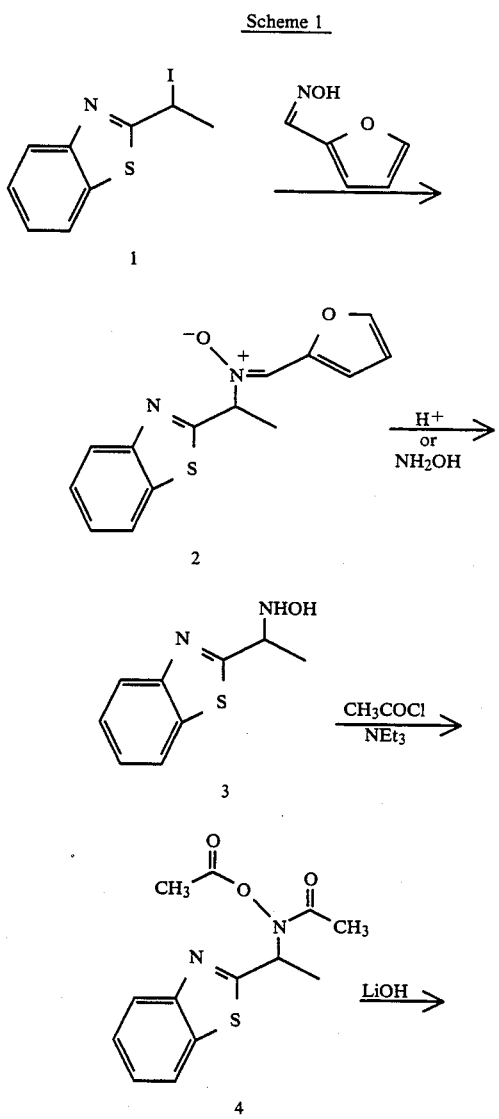

Scheme 1

-continued
Scheme 1

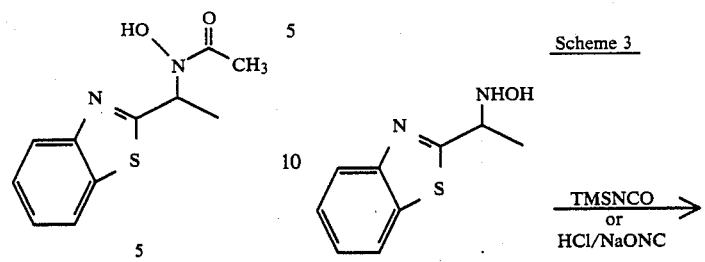

In scheme 1, iodide 1 is treated with Z-furfuraldehyde oxime and a base such as sodium methoxide to give nitrone 2. The nitrone is then hydrolyzed under acidic conditions or with hydroxylamine. The hydroxylamine 3 is then treated with acetylchloride in the presence of triethylamine to yield diacetate 4. The O-acetate is selectively removed by treatment with lithium hydroxide in isopropanol water to give the hydroxamic acid 5. Chlorides, bromides, tosylates and the like may be used in placed of iodide 1.

Hydroxylamine 3 can be converted to N-hydroxy ureas such as 7 as shown in scheme 2, below.

Scheme 2

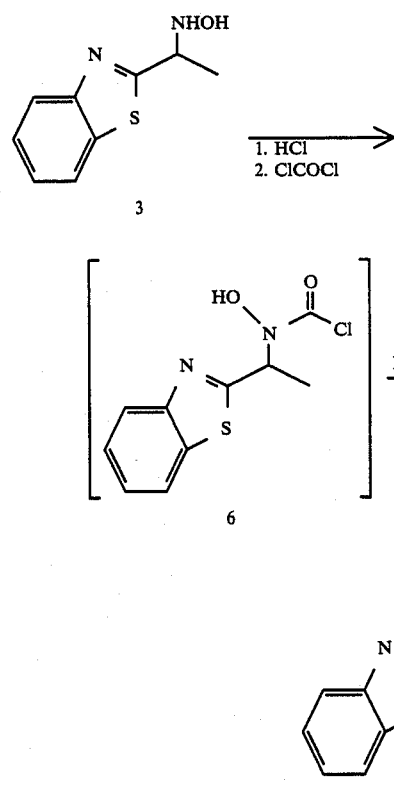

Hydroxylamine 3 is treated with gaseous HCl to form the hydrochloride salt, followed by phosgene to yield the putative intermediate 6. Without isolation 6 is treated with ammonium hydroxide to provide the hydroxyurea 7.

In addition to the method of scheme 2 above, ureas such as 7 can also be prepared from 3 using the method illustrated in scheme 3.

Scheme 3

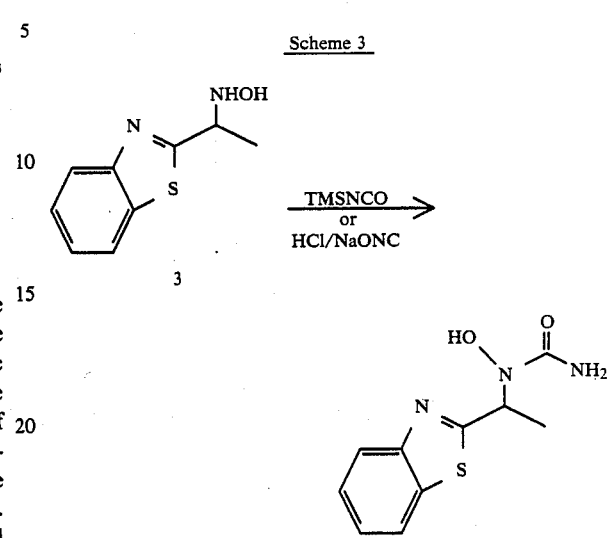

Hydroxylamine 3 is treated with trimethylsilyl isocyanate (TMSNCO), followed by ammonium chloride workup, to give 7. Alternatively 3 can be treated with sodium cyanate in an acidic solution to yield 7.

In addition to the methods described above, N-hydroxy ureas such as 7 and hydroxamic acids such as 5 can be prepared as shown in scheme 4, below.

Scheme 4

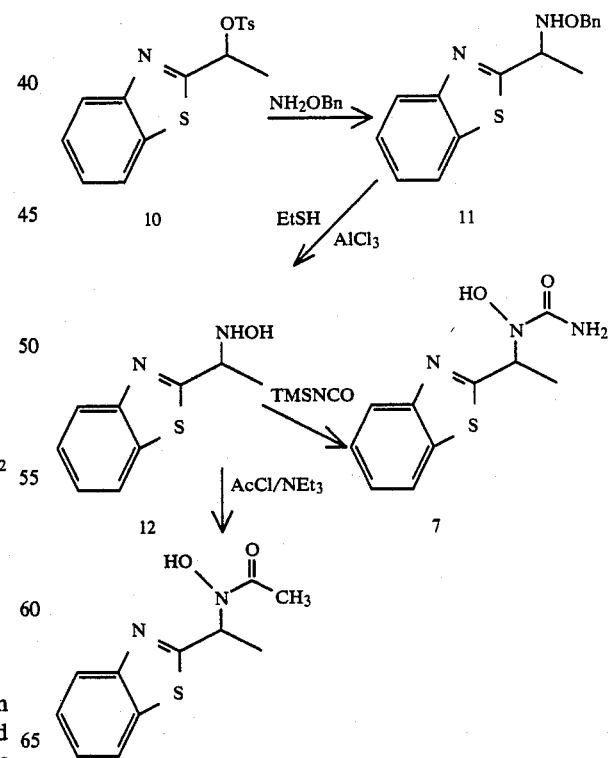

Tosylate 10 is heated with O-benzylhydroxylamine in a solvent such as dimethylsulfoxide or tetrahydrofuran to yield the new hydroxylamine 11. The benzyl protecting group can be removed by treatment with alumimum chloride and ethanethiol to give hydroxylamine 12. This can either be reacted with trimethylsilylisocyanate or NaNCO/HCl as depicted in schemes 2 and 3 to give 7 or with acetyl chloride to give 5, as shown in scheme 1. In some cases the benzyl group may be removed by reduction with palladium on carbon and hydrogen. Other O-protected hydroxylamines may also be use, e.g. O-methylhydroxylamine or O-tetrahydropyranylhydroxylamine.

In addition to the methods shown in scheme 4, O-protected hydroxylamines, such as 11 may be prepared as illustrated in scheme 5, below.

Scheme 5

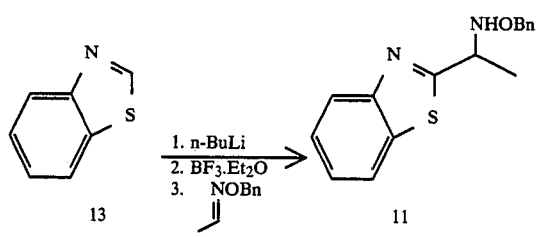

Benzthiazole 13, is treated with n-butyl lithium followed by boron trifluoride etherate. This is then reacted with O-benzylacetaldehyde oxime to yield the protected hydroxylamine, 11. This may be converted to compounds such as 5 to 7 as described in scheme 4.

The following examples further illustrate the synthesis and use of compounds of this invention. The appropriate designations for $R_1$, A, X and Y as defined by formula I are given for each example below.

EXAMPLE 1

N-hydroxy-N-(1-methyl-benzo[b]imidazol-2-ylmethyl)N'-methylurea a. Nitrone Intermediate. Sodium ethoxide was added to an ethanol solution of Z-furfuraldehyde oxime (0.11 g, 1.04 mmole) and allowed to be stirred for 45 minutes. An ethanol solution of 1-methyl-2-chloromethylbenzo[b]imidazole (0.188 g, 1.04 mmole) was added to the above solution and the mixture stirred for 2 hours. The solution was concentrated to dryness and the residue partitioned between ethyl acetate and water. The organic layer was washed with water, dried with MgSO4 and concentrated to a solid. The solid was washed with 1:1 ether/hexanes to give the desired product as a white solid (0.11 g, 44%).

b. 1-Methyl-benzo[b]imidazol-2-yl methyl hydroxylamine. The nitrone (0.53 g, 2.1 mmole) prepared as described in step a above and hydroxylamine (~15 mmole) were stirred at room temperature for 90 minutes in a methanol solution. The reaction mixture was concentrated to dryness and the residue titurated with THF to remove hydroxylamine. Pentane was added to the THF solution to precipitate the desired product which was used without further purification.

c. N-Hydroxy-N-(1-methyl-benzo[b]imidazol-2-ylmethyl)urea. The hydroxylamine (2.1 mmole) prepared as described in step b above and methyl isocyanate (0.178 g, 0.184 mL) were stirred together for two hours in THF. The solvent was removed and the residue washed with ether and methanol to give the desired compound as a white solid (0.1 g). ($R_1$=NHCH$_3$, A=—CH$_2$—, X=NCH$_3$, Y=H).

Melting Point: 145°–147° C.

NMR (300 MHz, DMSO-d$_6$): 2.64 (d, J=4.5 Hz, 3H); 3.78 (s, 3H); 4.81 (s, 2H); 7.08 (m, 1H); 7.21 (m, 2H); 7.52 (m, 1H); 7.59 (m, 1H); 9.39 (s, 1H).

Mass spectrum (CI—NH$_3$): 235 (M+1)$^+$.

EXAMPLE 2

N-hydroxy-N-(1-benzo[b]thiazol-2-ylethyl)urea a. N-Benzyloxy-1-benzothiazo-2-ylethylamine. To a stirred solution of benzthiazole (3.7 g, 27.4 mmole) in THF (200 mL) under an argon atmosphere at 78° C. was added n-butyl lithium (28.7 mmole, 11.5 mL, 2.5M in hexanes) via syringe. The mixture was stirred 0.5 h at −78° C. Boron trifluoride etherate (4.1 g, 38.7 mmole) was then added via syringe to the cold stirred solution. O-benzylacetaldehyde oxime (4.5 g, 30.2 mmole) was added immediately and the mixture stirred for 1 h at −78° C. The reaction was then quenched with aqueous NH$_4$Cl (20 mL) at −78° C. and the ice bath removed. The mixture was concentrated and the residue partitioned between ether and water. The organic layer was dried over MgSO$_4$ and concentrated. Purification of the residue by flash column chromotography on silica gel, eluting with 15% ethyl acetate in hexanes gave a yellow oil (2.8 g, 36%).

b. 1-Benzothiazo-2-ylethylhydroxylamine. Ethane thiol (30 mL) was cooled to 0° C. under argon and aluminum chloride (9.23 g, 69.2 mmole) was added in three portions while stirring. The mixture stirred for 10 min at 0° C. The N-benyzloxy-1-benzothiazo-2-ylethylamine prepared as described in step a above (2.8 g, 9.9 mmole) in CH$_2$Cl$_2$ (10 mL) was added dropwise to the above solution. The ice bath was removed and the mixture stirred overnight. The solution was then poured onto ice (100 g), diluted with water, and extracted thoroughly with ethyl acetate. The aqueous layer was neutralized with 3N NaOH and extracted with CH$_2$Cl$_2$ (2×50 mL). The organic extracts were combined with the ethyl acetate layer from above, dried with MgSO$_4$ and concentrated in vacuo. The residue was recrystallized from ethyl acetate/hexane giving a white solid (0.94 g) The mother liquor was concentrated and the residue chromatographed on silica gel eluting with 50% ethyl acetate in hexanes to give an additional 0.6 g. Total yield of the desired material was 1.54 g (81%).

c. N-hydroxy-N-(1-benzo[b]thiazol-2-ylethyl)urea. The desired material was prepared as described in example 1, step c, except using the material prepared as in step b, above and using trimethylsilyl isocyanate instead of methyl isocyanate. ($R_1$=NH$_2$, A=CHCH$_3$—, X=S, Y=H).

Melting Point: 159°–160° C.

NMR (300 MHz, DMSO-d$_6$): 1.58 (d, J=7.6 Hz, 3H); 5.56 (q, J=7.6 Hz, 1H); 7.45 (m, 2H); 7.96 (m, 1H); 8.08 (m, 1H); 9.46 (s, 1H).

Mass spectrum (CI—NH$_3$); 238 (M+1)$^+$, 222, 164.

Analysis (C$_{10}$H$_{11}$N$_3$O$_2$S): Calculated—C: 50.62, H: 4.67, N: 17.71; Found C: 50.50, H: 4.68, N: 17.61.

EXAMPLE 3

N-hydroxy-N-(1-benzo[b]oxazol-2-ylethyl)urea a. 2-Acetylbenzoxazole. Methyl magnesium bromide (6. mL, 3.0M in ether) was added to a solution of 2-cyanobenzoxazole (2.0 g) and CuBr (~5 mg) in ether. The resulting brown suspension was stirred for 1 hour and poured into 3N HCl. The organic layer was dried over $MgSO_4$ and concentrated in vacuo to give a brown solid (1.7 g).

b. 1-Benzoxazol-2-ylethanol. Diisobutyl aluminum hydride (36 mL, 1.0M in $CH_2Cl_2$) was added to a solution of 2-acetylbenzoxazole (2.9 g), prepared as described in step a above, in $CH_2Cl_2$. The mixture was stirred for 3 hours and then quenched by the addition of methanol. 2N HCl (50 mL) was added at 0° and the mixture was stirred for 30 minutes. The aluminum salts were filtered off, the layers separated and the aqueous layer re-extracted with ether. The combined organic layers were dried with $MgSO_4$ and concentrated to yield the desired product.

c. 1-Toluenesulfonyl 1-benzoxazol-2-ylethane. Toluene sulfonyl chloride (0.6 g, 3.1 mmole) was added to a solution of 1-benzoxazol-2-ylethanol (0.5 g, 3.06 mmole) prepared as described in step b above, and triethyl amine (0.45 g, 3.22 mmole) in $CH_2Cl_2$. The reaction mixture was stirred at room temperature for 20 hours and then refluxed for 2 hours. The mixture was extracted with 1N HCl, sodium bicarbonate and saturated NaCl solutions. After being dried over $MgSO_4$ the solvent was removed in vacuo. The resulting residue was chromatographed on 60 g of silica gel eluting with 2:1 $CH_2Cl_2$/pentane.

c. N-benzyloxy-1-benzoxazol-2-ylethylamine. O-benzylhydroxylamine (2.16 g, 17.6 mmole) was added to a solution of 1-toluenesulfonyl 1-benzoxazol-2-ylethane (1.8 g 5.67 mmole) prepared as described above in step c in DMF. The mixture was stirred at 50° C. for 2 days and then cooled and partitioned between hexane and 1N HCl. The organic layer was extracted twice with hexane and then all hexane fractions were combined and evaportated. The residue was chromatographed on 60 g silica gel eluting with 2:3 $CH_2Cl_2$/pentane. 250 mg of the desired product was d. N-hydroxy-1-benzoxazol-2-ylethylamine. Aluminum chloride (200 mg) was added to a solution of ethanethiol (4 mL). After this was stirred for 15 minutes at 0°, a solution of N-benzyloxy-1-benzoxazol-2-ylethylamine (68 mg) in $CH_2Cl_2$ (2 mL) was added dropwise and stirred an additional 2.5 hours at room temperature. The reaction was quenched with the addition of ice followed by 1N HCl. The mixture was brought to neutrality with 2N NaOH and extracted with ether. After being dried with $MgSO_4$ the solvent was removed in vacuo. The residue was chromatographed on silica e. N-hydroxy-N-(1-benzo[b]oxazol-2-ylethyl)urea. The desired material was prepared as described in example 1, except using N-hydroxy-1-benzoxazol-2-ylethylamine, prepared as described in step d above, instead of N-hydroxy-N-1-benzo[b]thiazol-2-ylethylamine. ($R_1=NH_2$, $A=$—$CHCH_3$—, $X=O$, $Y=H$).

NMR (300 MHz, DMSO-$d_6$): 1.55 (d, 3H, J=6.6 Hz); 4.68 (q, 1H, J=6.6 Hz); 6.78-7.00 m, 4H); 7.41 (br s, 1H); 8.2-8.6 (br s, 2H).

Mass spectrum (CI—$NH_3$): 222 $(M+1)^+$, 239 $(M+NH_4)^+$.

EXAMPLE 4

N-hydroxy-N-(1-benzo[b]thiazol-2-ylethyl)acetamide

The desired material is prepared as described in example 1, except using acetyl chloride and triethyl amine instead of trimethylsilyl isocyanate. ($R_1=CH_3$, $A=CHCH_3$—, $X=S$, Examples 5-28 are prepared in a manner generally analogous to the methods described in examples 1-4 above or as in schemes 1-5.

EXAMPLE 5

N-hydroxy-N-(benzo[b]oxazol-2-ylmethyl)N'-1-methylethyl urea ($R_1=NHCH(CH_3)_2$, $A=$—$CH_2$—, $X=O$, $Y=H$).

EXAMPLE 6

N-hydroxy-N-(1-benzo[b]oxazol-2-ylethyl)N',N'-dimethyl urea ($R_1=N(CH_3)_2$, $A=$—$CHCH_3$—, $X=O$, $Y=H$).

EXAMPLE 7

N,N'-dihydroxy-N-(1-benzo[b]oxazol-2-ylethyl)urea ($R_1=NHOH$, $A=$—$CHCH_3$—, $X=O$, $Y=H$).

EXAMPLE 8

N-hydroxy-N-(benzo[b]oxazol-2-ylmethyl)methylpropionamide ($R_1=CH(CH_3)_2$, $A=$—$CH_2$—, $X=O$, $Y=H$).

EXAMPLE 9

N-hydroxy-N-[(1-ethylbenzo[b]imidazol-2-yl)methyl]propenamide ($R_1=CH=CH_2$, $A=$—$CH_2$—, $X=NCH_2CH_3$, $Y=H$).

EXAMPLE 10

N-hydroxy-N-(1-methyl-1-benzo[b]oxazol-2-ylethyl)urea ($R_1=NH_2$, $A=$—$C(CH_3)_2$—, $X=O$, $Y=H$).

EXAMPLE 11

N-hydroxy-N-(2-benzo[b]oxazol-2-ylethyl)urea ($R_1=NH_2$, $A=$—$CH_2CH_2$—, $X=O$, $Y=H$).

EXAMPLE 12

N-hydroxy-N-(1-methylethyl-2-benzo[b]oxazol-2-ylethyl)acetamide ($R_1=CH_3$, $A=$—$CH_2CH(CH(CH_3)_2)$—, $X=O$, $Y=H$).

EXAMPLE 13

N-hydroxy-N-[3-(6-phenoxybenzo[b]oxazol-2-yl)propyl]urea ($R_1=NH_2$, $A=$—$CH_2CH_2CH_2$—, $X=O$, $Y=6$—$C_6H_5O$).

EXAMPLE 14

N-hydroxy-N-(3-benzo[b]thiazol-2-yl prop -2-enyl)urea ($R_1=NH_2$, $A=$—$CH=CHCH_2$—, $X=S$, $Y=H$).

EXAMPLE 15

N-hydroxy-N-(1-methyl-3-benzo[b]oxazol-2-ylprop-2-enyl)urea ($R_1=NH_2$, $A$—$CH=CHCHCH_3$—, $X=O$, $Y=H$).

EXAMPLE 16

N-hydroxy-N-[1-(4-methoxy-benzo[b]imidazol-2-yl)ethyl]urea ($R_1=NH_2$, $A=$—$CHCH_3$—, $X=NH$, $Y=4$—$OCH_3$).

EXAMPLE 17

N-hydroxy-N-[1-(1-acetylbenzo[b]imidazol-2-yl)ethyl]urea ($R_1$=$NH_2$, A=—$CHCH_3$—, X=$NCOCH_3$, Y=H).

EXAMPLE 18

N-hydroxy-N-[1-(1-benzoylbenzo[b]imidazol-2-yl)ethyl]urea ($R_1$=$NH_2$, A=—$CHCH_3$—, X=$NCOC_6H_5$, Y=H).

EXAMPLE 19

N-hydroxy-N-(1-benzo[b]thiazol-2-ylethyl)urea 3,3-dioxide ($R_1$=$NH_2$, A=—$CHCH_3$—, X=$SO_2$, Y=H).

EXAMPLE 20

N-hydroxy-N-[1-(5-fluorobenzo[b]oxazol-2-yl)ethyl]urea ($R_1$=$NH_2$, A=—$CHCH_3$—, X=O, Y=5—F).

EXAMPLE 21

N-hydroxy-N-[1-(7-hydroxybenzo[b]oxazol-2-yl)ethyl]urea ($R_1$=$NH_2$, A=—$CHCH_3$—, X=O, Y=7—OH).

EXAMPLE 22

N-hydroxy-N-[6-trifluoromethyl-(1-benzo[b]oxazol-2-yl)ethyl]urea ($R_1$=$NH_2$, A=—$CHCH_3$—, X=O, Y=6—$CF_3$).

EXAMPLE 23

N-hydroxy-N-[1-(5,6-dimethylbenzo[b]oxazol-2-yl)ethyl]urea ($R_1$=$NH_2$, A=—$CHCH_3$—, X=O, Y=5,6—$(CH_3)_2$).

EXAMPLE 24

N-hydroxy-N-[1-(6-(4-fluorophenyl)benzo[b]thiazol-2-yl)ethyl]urea ($R_1$=$NH_2$, A=—$CHCH_3$—, X=S, Y=6—(4—F—$C_6H_4$)).

EXAMPLE 25

N-hydroxy-N-[1-(5-phenylmethoxybenzo[b]oxazol-2-yl)ethyl]urea ($R_1$=$NH_2$, A=—$CHCH_3$—, X=O, Y=5—$C_6H_5CH_2O$).

EXAMPLE 26

N-hydroxy-N-(6-phenylmethylbenzo[b]thiazol-2-ylmethyl)N'-methyl urea ($R_1$=$NHCH_3$, A=—$CH_2$—, X=S, Y=6—$C_6H_5CH_2$).

EXAMPLE 27

N-hydroxy-N-[4-(3,5-bistrifluoromethylbenzoyl)-1-benzo[b]oxazol-2-ylethyl]urea ($R_1$=$NH_2$, A=—$CHCH_3$—, X=O, Y=4-(3,5—$CF_3$—$C_6H_3CO$).

EXAMPLE 28

N-hydroxy-N-(1-benzo[b]thiazol-2-ylethyl)urea sodium salt

The material prepared as in example 2 is dissolved in tetrahydrofuran and one equivalent of sodium hydride is added. Hexane is added and the desired product collected by filtration. ($R_1$=$NH_2$, A=—$CHCH_3$—, X=S, Y=H, M=Na).

EXAMPLE 29

N-hydroxy-N-(1-benzo[b]thiazol-2-ylethyl)urea ammonium salt

The material prepared as in example 2 is dissolved in tetrahydrofuran and ammonia is bubbled through the solution. Hexane is added and the desired product collected by filtration. ($R_1$=$NH_2$, A=—$CHCH_3$—, X=S, Y=H, M=$NH_4$).

EXAMPLE 30

N-hydroxy-N-(1-benzo[b]thiazol-2-ylethyl)urea tetrabutylammonium salt

The material prepared as in example 2 is dissolved in tetrahydrofuran and one equivalent of tetrabutyl ammonium hydroxide is added. After hydrogen evolution ceases, hexane is added and the desired product collected by filtration. ($R_1$=$NH_2$, A=—$CHCH_3$—, X=S, Y=H, M=$N(C_4H_9)_4$).

EXAMPLE 31

N-butoxy-N-(1-benzo[b]thiazol-2-ylethyl)urea

The material prepared as in example 2 and 1.1 equivalents of triethylamine are dissolved in tetrahydrofuran and 1 equivalent of butyryl chloride is added. Ether is added and the material is washed with 2N HCl, dried with $MgSO_4$ and the evaporated to yield the desired product. ($R_1$=$NH_2$, A=—$CHCH_3$—, X=S, Y=H,

EXAMPLE 32

Lipoxygenase $IC_{50}$ Determination

Assays to determine 5-lipoxygenase activity were performed in 200 $\mu L$ incubations containing the 20,000×g supernatant from 6×$10^4$ homogenized RBL-1 cells, 2% DMSO vehicle and various concentrations of the test compound. Reactions were initiated by addition of radiolabelled arachidonic acid and terminated by acidification and ether extraction. Reaction products were separated from nonconverted substrate by thin layer chromatography and measured by liquid scintillation spectroscopy. All treatments were evaluated in triplicate incubations. Inhibition of 5-lipoxygenase activity was computed by comparison of the quantity of products formed in the treatment incubations to the mean product formation in vehicle control groups (n=8). $IC_{50}$ values and 95% confidence limits were computed by linear regression analysis of percentage inhibition versus log inhibitor concentration plots. The results of the assay indicate that the compounds are inhibitors of 5-lipoxygenase.

TABLE 1

In vitro 5-lipoxygenase inhibitory potency of compounds of this invention.

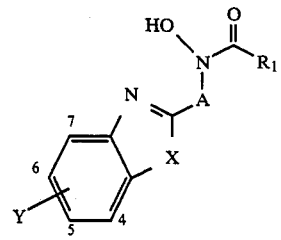

| Example | $R_1$ | A | X | Y | $IC_{50}(\mu M)$ |
|---------|-------|---|---|---|------------------|
| 1 | $NHCH_3$ | —$CH_2$— | $NCH_3$ | H | 85 |
| 2 | $NH_2$ | —$CHCH_3$— | S | H | 1.9 |

The foregoing is merely illustrative of the invention and is not intended to limit the invention to the disclosed compounds. Variations and changes which are

What is claimed is:

1. A compound of the formula:

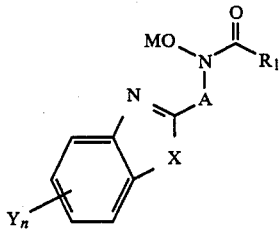

wherein $R_1$ is (1) hydrogen, (2) $C_1$ to $C_4$ alkyl, (3) $C_2$ to $C_4$ alkenyl, (4) $NR_2R_3$, wherein $R_2$ and $R_3$ are independently selected from hydrogen, $C_1$ to $C_4$ alkyl and hydroxyl, but $R_2$ and $R_3$ are not simultaneously hydroxyl;

X is (1) oxygen, (2) sulfur, (3) $SO_2$, or (4) $NR_4$, wherein $R_4$ is (1) hydrogen, (2) $C_1$ to $C_6$ alkyl, (3) $C_1$ to $C_6$ alkoyl or (4) aroyl;

A is selected from $C_1$ to $C_6$ alkylene or $C_2$ and $C_6$ alkenylene; n is 0–4;

Y is independently selected at each occurrence from (1) hydrogen, (2) halogen, (3) hydroxy, (4) cyano, (5) halosubstituted alkyl, (6) $C_1$ to $C_{12}$ alkyl, (7) $C_2$ to $C_{12}$ alkenyl, (8) $C_1$ to $C_{12}$ alkoxy, (9) $C_3$ to $C_8$ cycloalkyl, (10) aryl, (11) aryloxy, (12) aroyl, (13) $C_1$ to $C_{12}$ arylalkyl, (14) $C_2$ to $C_{12}$ arylalkenyl, (15) $C_1$ to $C_{12}$ arylalkoxy, (16) $C_1$ to $C_{12}$ arylthioalkoxy, and substituted derivatives of (17) aryl, (18) aryloxy, (19) aroyl, (20) $C_1$ to $C_{12}$ arylalkyl, (21) $C_2$ to $C_{12}$ arylalkenyl, (22) $C_1$ to $C_{12}$ arylalkoxy, (23) $C_1$ to $C_{12}$ arylthioalkoxy, wherein substituents are selected from halo, nitro, cyano, $C_1$ to $C_{12}$ alkyl, alkoxy, and halosubstituted alkyl;

and M is hydrogen, a pharmaceutically acceptable cation, aroyl, or $C_1$ or $C_{12}$ alkoyl.

2. A compound according to claim 1 wherein $R_1$ is $CH_3$.

3. A compound according to claim 1 wherein $R_1$ is $NH_2$.

4. A compound according to claim 1 wherein A is $-CHCH_3-$.

5. A compound according to claim 1 wherein X is oxygen, sulfur, or $NCH_3$.

6. A method for inhibiting 5- and/or 12-lipoxygenase activity comprising administering to a mammal in need of such treatmena therapeutically effective amount of a compound of the claim 1.

7. The method of claim 6 wherein $R_1$ is $CH_3$.

8. The method of claim 6 wherein $R_1$ is $NH_2$.

9. The method of claim 6 wherein A is $-CHCH_3-$.

10. The method of claim 6 wherein X is oxygen, sulfur, or $NCH_3$.

11. A method for treating diseases in which lipoxygenase enzymes are contributory, comprising administering to a human or lower animal in need of such treatment a therapeutically effective amount to inhibit lipoxygenase of a compound of the claim 1.

12. A pharmaceutical composition for inhibiting 5- and/or 12-lipoxygenase, comprising a pharmaceutical carrier and a therapeutically effective amount of a compound of claim 1.

* * * * *